United States Patent
Fache et al.

(10) Patent No.: US 6,214,190 B1
(45) Date of Patent: Apr. 10, 2001

(54) METHOD FOR SEPARATING A CATALYST BY MEMBRANE ELECTRODIALYSIS

(75) Inventors: Eric Fache, Villeurbanne; Dominique Horbez, Franconville; Philippe Leconte, Meyzieu, all of (FR)

(73) Assignee: Rhodia Fiber and Resin Intermediates, Courbevoie Cedex (FR)

(*) Notice: Subject to any disclaimer, the term of this patent is extended or adjusted under 35 U.S.C. 154(b) by 0 days.

(21) Appl. No.: 09/155,597

(22) PCT Filed: Mar. 27, 1997

(86) PCT No.: PCT/FR97/00559

§ 371 Date: Feb. 8, 1999

§ 102(e) Date: Feb. 8, 1999

(87) PCT Pub. No.: WO97/36673

PCT Pub. Date: Oct. 9, 1997

(30) Foreign Application Priority Data

Apr. 2, 1996 (FR) .................................... 96 04379

(51) Int. Cl.[7] .................................... B01D 61/44
(52) U.S. Cl. .................... 204/529; 204/530; 204/531; 204/541
(58) Field of Search .................. 204/529, 530, 204/531, 541

(56) References Cited

U.S. PATENT DOCUMENTS

| | | | | |
|---|---|---|---|---|
| 3,673,068 | * | 6/1972 | Seko et al. | 204/531 |
| 4,680,098 | * | 7/1987 | Chang | 204/182.4 |
| 5,282,939 | * | 2/1994 | Voss | 204/531 |

FOREIGN PATENT DOCUMENTS

| | | |
|---|---|---|
| 19 54 707 | 5/1970 | (DE) . |
| 19 63 101 | 7/1970 | (DE) . |
| 2 722 783 | 1/1996 | (FR) . |

OTHER PUBLICATIONS

Desalination, vol. 79, No. 2 / 03, Dec. 1, 1990, pp. 233–247, XP000244545, Sridhar S: "Desalination and Recovery of Catalysts by Electrodialysis".

* cited by examiner

Primary Examiner—Arun S. Phasge
(74) Attorney, Agent, or Firm—Burns, Doane, Swecker & Mathis, L.L.P.

(57) ABSTRACT

The present invention relates to a process for isolating, by membrane electrodialysis, a catalyst from a solution containing it. More precisely, it relates to the isolation of a catalyst used in a homogeneous phase molecular oxidation reaction. The invention consists of a process for isolating a homogeneous catalyst dissolved in a mixture also containing at least one aliphatic diacid, characterized in that the catalyst contains cobalt and the isolation is performed by membrane electrodialysis.

14 Claims, No Drawings

METHOD FOR SEPARATING A CATALYST BY MEMBRANE ELECTRODIALYSIS

This applications is a 371 of PCT/FR97/00559 filed Mar. 27, 1997.

The present invention relates to a process for isolating, by membrane electrodialysis, a catalyst from a solution containing it.

More precisely, it relates to the isolation of a catalyst used in an oxidation reaction by means of molecular oxygen in homogeneous phase.

Oxidation processes using homogeneous catalysis are relatively numerous. Thus, the oxidation of cycloalkanes to corresponding diacids can be carried out by employing a soluble salt of heavy metals like cobalt or manganese.

U.S. Pat. No. 2,223,493, published in December 1940, describes the oxidation of cyclic hydrocarbons to corresponding diacids, in liquid phase generally containing acetic acid, at a temperature of at least 60° C., with the aid of a gas containing oxygen and in the presence of an oxidation catalyst such as a cobalt compound. This patent envisages an isolation of the adipic acid formed by crystallization, but does not teach anything about the manner of recycling the catalyst into a new oxidation operation, nor, with still greater reason, about the activity which a catalyst recycled one or more times would possess.

Patent FR-A-2 722 783 describes a process for isolating and recycling a cobalt catalyst which has been used for the oxidation of cyclohexane to adipic acid, after separation of the main reaction products and of at least a proportion of the acetic acid solvent from the reaction mixture. This process consists essentially in extracting most of the catalyst with the aid of cyclohexane or of a mixture of cyclohexane and acetic acid. This process is efficient and the recycled catalyst has not lost its activity. However, it involves large quantities of solvent and requires several successive operations.

It therefore appears desirable to have available a process for isolating a homogeneous catalyst dissolved in a reaction mixture, which is equally efficient while being simpler to implement.

Patent FR-A-1 591 176 describes a process for recovering metal catalysts and nitric acid which are present in the mother liquors resulting from the separation of the reaction mass obtained during the nitric oxidation of cyclohexanol and/or of cyclohexanone, consisting in passing a proportion of the mother liquors containing the metal salts, the nitric acid and the organic acids into an electrodialysis cell. The metal catalysts employed are copper salts or vanadium salts.

Patent FR-A-2 026 288 describes a process for recovering a large proportion of nitric acid and of metal ions from an acidic residual liquid produced during the manufacture of adipic acid by liquid phase oxidation of cyclohexanone or cyclohexanol, including the introduction of this liquid into an electrodialysis device consisting of one or more electrodialysers, to recover the nitric acid and the metal ions in a recovery liquid which may be water or a dilute solution of nitric acid. The metal catalysts employed are copper salts or vanadium salts.

These two processes are very similar, or even identical, and use solutions containing high concentrations of nitric acid. This particular feature considerably promotes the separation of the metal salts, in the form of nitrates, of the undissociated carboxylic acids.

The present invention relates to the isolation of a homogeneous catalyst used in the oxidation of cyclohexane with oxygen and therefore not comprising nitric acid.

It relates more precisely to a process for isolating a homogeneous catalyst dissolved in a mixture also containing at least one aliphatic diacid, characterized in that the catalyst contains cobalt and the isolation is performed by membrane electrodialysis.

The homogeneous catalysts are metal compounds usually employed for the oxidation of cycloalkanes to aliphatic diacids. They are more particularly catalysts containing cobalt, alone or with other metals such as manganese, copper, iron, vanadium or cerium or mixtures of these metals. These metals are in the form of compounds which are soluble in the reaction mixture for cycloalkane oxidation. Such compounds are hydroxides, oxides and organic or inorganic salts. The preferred compounds are cobalt salts, alone or in combination with other compounds based on metals such as manganese and/or copper and/or iron and/or cerium and/or vanadium.

Examples of these cobalt salts which may be mentioned are cobalt chloride, cobalt bromide, cobalt nitrate and cobalt carboxylates such as cobalt acetate, cobalt propionate, cobalt adipate, cobalt glutarate or cobalt succinate. Since one of the solvents most frequently employed for the oxidation of cycloalkanes is acetic acid, cobalt acetate tetrahydrate is particularly preferred.

The mixture subjected to the membrane electrodialysis contains at least one diacid formed during the oxidation of the cycloalkane and often one or more other diacids also formed as by-products. It may also contain all the by-products of the reaction. When the catalyst is employed for the oxidation of cyclohexane, adipic acid is obtained predominantly, but so are glutaric acid and succinic acid, as well as more or less considerable quantities of cyclohexanol, cyclohexanone, cyclohexyl esters, lactones and hydroxycarboxylic acids.

Although the oxidation reaction is generally carried out in an organic solvent, preferably acetic acid in the case of cyclohexane oxidation, or, where appropriate, without solvent, the mixture to be electrodialysed preferably contains water.

The mixture in which the homogeneous catalyst is to be found therefore preferably includes water, it being possible for the solvent which may have been used in the process which has produced the solution to be treated to be entirely or partially replaced with water before the electrodialysis. The water generally represents from 10% to 100% of the solvent mixture of the solution subjected to the electrodialysis and preferably from 50% to 100% of this solvent mixture.

In its outline, electrodialysis is a process which, under the effect of a direct electrical field, enables the ionized species present in the solution to be treated to be extracted by migration through ion exchange membranes.

The electrodialysis apparatus used consists of various compartments bounded alternately by cationic membranes and anionic membranes. These compartments are divided into dilution compartments (D) which become depleted in compound to be isolated, that is to say in catalyst in the process of the invention, and concentration compartments (C) which, in contrast, become enriched in compound to be isolated.

In fact, under the action of the electrical field the cations in the solution to be treated migrate towards the cathode, leaving the compartment (D) where they are to be found, through a cation exchange membrane (cationic membrane). When they have moved into the next compartment (C), they cannot leave it because of the presence of the next anion exchange membrane (anionic membrane). Simultaneously, the anions migrate towards the anode, passing through an anionic membrane and enter an adjacent compartment (C), which they cannot subsequently leave because of the presence of the next cationic membrane.

Two adjacent compartments (C) and (D) form an electrodialysis cell. An electrodialyser comprises a stack of a number of cells. This number of cells per electrodialyser is generally as high as possible. For example, this number can advantageously vary between 10 and 500 cells.

In practice the anionic and cationic membranes are placed alternately in a system of filter-press type.

The homopolar membranes employed in the process of the invention are divided up into two large classes, according to their method of manufacture.

They are, first of all, heterogeneous membranes, prepared from ion exchange resins mixed with a binder such as polyvinyl chloride, polyethylene or the like. The combination thus formed can coat a screen like, for example, a polyester or polyacrylonitrile fabric.

They are also homogeneous membranes, obtained by introducing a functional group onto an inert support by chemical or radiochemical grafting. The chemical method, more widely employed, generally consists in functionalizing a latex of a polymer containing aromatic nuclei, such as styrene/divinylbenzene or styrene/butadiene. Thus functionalized, the latex is then used to coat a screen as in the case of the heterogeneous membranes. The radiochemical method generally comprises the grafting, under the influence of a radiation, of an aromatic compound such as styrene, onto an inert support like a sheet of polyethylene or of polytetrafluoroethylene. The aromatic nucleus is subsequently functionalized as in the chemical method.

The cation exchange membranes (cationic membranes) comprise strong acidic groups, in most cases sulphonate groups, or weakly acidic groups, frequently carboxylate groups. More rarely the acidic groups may be $PO_3^{2-}$, $HPO_2^-$, $AsO_3^{2-}$ and $SeO_3^-$ groups.

The anion exchange membranes (anionic membranes) comprise strong basic groups, in most cases quaternary ammonium groups, or weak basic groups, in most cases amine groups. More rarely, the basic groups may be quaternary phosphonium groups or sulphonium groups.

In the present process the cationic membranes preferably comprise strong acidic groups and among these preferentially sulphonate groups, and the anionic membranes preferably comprise strong basic groups and among these preferentially quaternary ammonium groups.

Besides the membranes the electrodialyser comprises, of course, a cathode and an anode. The anode consists of materials conventionally employed in electrodialysis, for example graphite, titanium coated with precious metals or precious metal oxides, especially platinum-coated titanium. The cathode also consists of materials conventionally employed in electrodialysis, for example graphite, stainless steel or nickel.

The electrodialyser is fed with the solution to be treated, which is at least partially aqueous. It is also necessary to circulate an anolyte solution at the anode and a catholyte solution at the cathode. These solutions frequently constitute a single electrolyte solution. In the present process a single electrolyte circuit is very suitable. The function of the electrolyte solution is to ensure a sufficient conductivity. This conductivity will preferably be equal to or higher than 20 millisiemens per centimetre (mS/cm), without this lower limit being considered to be critical for the implementation of the present process.

The electrolyte used is an ionizable compound such as a salt, an acid or a base. The electrolyte is preferably chosen from nonelectroactive compounds. Thus, for example, on an industrial scale it is preferable not to employ chlorides, which would generate chlorine at the anode.

Examples of electrolytes which may be mentioned are neutral salts like sulphates, acids like sulphamic acid, water-soluble carboxylic acids and sulphuric acid. A salt of the catalyst metal, more particularly a cobalt salt such as, for example, cobalt acetate, can also be employed as electrolyte.

In the present process it will be necessary to avoid using electrolyte solutions whose pH could result in the precipitation of the metal compound which it is desired to isolate by electrodialysis. This is why an acidic electrolyte will preferably be chosen.

The voltage applied to the electrodialyser must be such as to avoid the polarization of the system, that is to say dissociation of the water under the effect of an excessively intense electrical field. In general a voltage of 0.5 volt to 2.5 volt/cell and preferably of 0.5 volt to 1.5 volt/cell is appropriate. The polarization effect can be decreased by increasing the turbulence of the liquid by the use of thin cells together with separating frames. Cells which have a width of 0.5 mm to 2 mm and preferably from 0.75 mm to 1.5 mm are preferred.

The temperature at which the process of the invention is carried out is situated in a region that is compatible with the stability of the membranes. In fact, while, in principle, elevated temperatures are favourable, increasing the electrolyte mobility and reducing the viscosity of the solution to be treated, the increase in the temperature shortens the lifetime of the membranes. The operation will therefore preferably be carried out at a temperature lower than or equal to 50° C. and more particularly between 20° C. and 40° C.

The electrodialyser can operate in various ways. It may, first of all, operate continuously (straight-through operation), the solution to be treated passing continuously through the stack; a number of stages are then arranged in series if the degree of treatment to be obtained requires it. It may also operate noncontinuously (operation with recirculation), the solution to be treated recirculating in a cell until the desired degree of treatment is obtained. Finally, it may operate straight through with partial recirculation.

The reaction mixture in which the homogeneous catalyst to be isolated is present, together with the diacids, originates essentially, as already stated, from the processes for oxidation of cycloalkanes to the corresponding diacids. To simplify matters, in the description which follows, the oxidation of cyclohexane to adipic acid will be generally considered, resulting in the formation of smaller, but nevertheless large, quantities of glutaric acid and of succinic acid.

Before treating such a mixture by electrodialysis it is generally advantageous to carry out some operations allowing in particular most of the adipic acid to be isolated, this being the compound whose preparation is aimed at.

This isolation may be performed in a known manner, for example by precipitating adipic acid by cooling this mixture.

The remaining solution is then taken up with water, optionally after a partial or complete removal of the organic solvent which it may contain, in order to be subjected to the electrodialysis according to the invention.

The solution which is electrodialysed generally contains from 0.0001 mole to 1 mole of catalyst per kilogram, from 0.001 mole to 1 mole of glutaric acid per kilogram, from 0.001 mole to 1 mole of succinic acid per kilogram and from 0.001 mole to 1 mole of adipic acid per kilogram.

The examples which follow illustrate the invention.

EXAMPLE 1

The electrodialyser employed consists of a stack of 10 cells of 2 dm² active area, each made up of a compartment where the solution to be treated is introduced (compartment D where the said solution will be dilute in catalyst) and of a compartment C which will receive the catalyst during the electrodialysis.

The membranes separating each compartment D from the adjacent compartment C are:
- anionic membrane of Neosepta AMX brand with quaternary ammonium groups,
- cationic membrane of Neosepta CMX brand with sulphonate groups.

The electrolyte consists of an aqueous solution of sulphamic acid which has a conductivity of 20 mS/cm at 20° C. The circulation flow rate of this solution is 400 l/h and its volume is 2 l.

The aqueous solution to be treated has a volume of 1.6 l and initially it contains:

0.18 mol/kg of adipic acid 0.87 mol/kg of glutaric acid 0.36 mol/kg of succinic acid 0.27 mol/kg of cobalt in the form of cobalt acetate.

The noncontinuous operating method (operation with recirculation) has been employed.

The circulation flow rate of this solution in compartments D is 180 l/h.

The solution which flows in the compartments C and which will receive the cobalt salt is initially an aqueous solution of sodium chloride at a concentration of 5 g/l; it has a volume of 1.6 l and it flows at a flow rate of 180 l/h.

The initial conductivity of each of the solutions of the compartments C is 10 mS/cm.

The electrodialysis is conducted at an applied voltage of 18 V.

Samples of the various solutions are taken at regular intervals in order to follow the progress of the operation. Cobalt is determined by atomic absorption and the diacids by vapour phase chromatography. The pH, the conductivity and the volume of the solutions are also followed.

Table 1 below collates the results of the measurements relating to the pH, the conductivity and the volume of the solutions.

Table 2 below collates the results relating to the concentrations in mol/kg of the various samples. By definition, L1 denotes the solution from compartments D, also called feed solution, L2 denotes the solution from compartments C, also called concentrated solution, and L3 denotes the electrolyte solution.

As can be ascertained in the results of Table 1, the feed solution becomes depleted in water; this is explained by the fact that the ions which migrate are hydrated and that at the end of the test the difference in conductivity between the feed solution and the concentrated solution is considerable (osmosis phenomenon).

To establish precise balances, the results will be expressed in Table 2, account being taken of the changes in volume. The results in Table 2 are expressed on the assumption that initially there is 1 kg of flow to be treated.

The symbol "–" in the table means that the measurement was not performed.

TABLE 1

| Time in min | Solution sampled | Temperature in °C. | pH | Conductivity in mS/cm | Volume in ml |
|---|---|---|---|---|---|
| 0 | L1 | 20.0 | 3.5 | 10.7 | 1600 |
| 0 | L2 | 20.0 | 4.6 | 10.1 | 1600 |
| 0 | L3 | 20.0 | — | 20.0 | 2000 |
| 18 | L1 | — | 3.5 | 9.6 | 1567 |
| 20 | L2 | — | 4.7 | 14.1 | 1639 |
| 38 | L1 | — | 3.2 | 7.6 | 1530 |
| 40 | L2 | 27.2 | 4.7 | 16.4 | 1677 |
| 57 | L1 | 28.4 | 2.9 | 5.1 | 1495 |
| 58 | L2 | — | 4.9 | 17.8 | 1712 |
| 80 | L1 | — | 2.1 | 1.9 | 1416 |
| 80 | L2 | — | 4.8 | 18.8 | 1793 |
| 86 | L1 | 30.2 | 2.0 | 1.8 | 1405 |
| 86 | L2 | — | 4.8 | 18.9 | 1805 |

TABLE 2

| Time in min | Solution sampled | Co in mol/kg | Adipic acid in mol/kg | Glutaric acid in mol/kg | Succinic acid in mol/kg |
|---|---|---|---|---|---|
| 0 | L1 | 0.267 | 0.183 | 0.869 | 0.355 |
| 0 | L2 | 0 | 0 | 0 | 0 |
| 0 | L3 | 0 | 0 | 0 | 0 |
| 0 | total | 0.267 | 0.183 | 0.869 | 0.355 |
| 18 | L1 | 0.192 | 0.184 | 0.867 | 0.340 |
| 20 | L2 | 0.066 | 0 | 0 | 0.002 |
| 20 | total | 0.258 | 0.184 | 0.867 | 0.342 |
| 38 | L1 | 0.137 | 0.175 | 0.822 | 0.316 |
| 40 | L2 | 0.127 | 0.005 | 0.050 | 0.036 |
| 40 | total | 0.264 | 0.180 | 0.872 | 0.352 |
| 57 | L1 | 0.064 | 0.174 | 0.827 | 0.306 |
| 58 | L2 | 0.193 | 0 | 0.044 | 0.076 |
| 58 | total | 0.257 | 0.174 | 0.871 | 0.382 |
| 80 | L1 | 0.005 | 0.149 | 0.753 | 0.271 |
| 80 | L2 | 0.251 | 0 | 0.082 | 0.080 |
| 80 | total | 0.256 | 0.149 | 0.835 | 0.351 |
| 86 | L1 | 0.0005 | 0.163 | 0.774 | 0.269 |
| 86 | L2 | 0.244 | 0 | 0.081 | 0.078 |
| 86 | L3 | 0.001 | 0 | 0 | 0.004 |
| 86 | total | 0.245 | 0.163 | 0.855 | 0.351 |

EXAMPLE 2

Oxidation of Cyclohexane to Adipic Acid

The aim in this example is to prepare a solution to be used in the process for isolating the catalyst by electrodialysis.

Into a jacketed 1.5-litre autoclave, made of titanium and equipped with a turbine and various openings for introducing reactants and fluids or for removing the reaction products and fluids, are charged, at ambient temperature, after the apparatus has first been purged with nitrogen:

| | |
|---|---|
| Co acetate tetrahydrate: | 4.0 g |
| acetic acid: | 359 g |
| cyclohexane: | 289.7 g |
| acetaldehyde: | 1.2 g |

After closing the autoclave the nitrogen pressure is raised to 20 bar (2 MPa), stirring is started (800 rev/min) and the temperature is raised to 120° C. over 29 minutes. The nitrogen is then replaced with 20 bar of air containing 4% of oxygen. The exit gas flow rate is controlled at 250 litres/hour.

After an induction period of 10 min, during which there is no oxygen consumption, the temperature rises abruptly to 106° C. and oxygen begins to be consumed. The oxygen content of the air at the entry is raised to 16% with the aid of a system of flowmeters. The oxygen content at the exit of the autoclave remains lower than 5% throughout the test. The average temperature in the autoclave is maintained at 106–107° C.

When 50 litres of oxygen have been consumed (which corresponds to a cyclohexane conversion of approximately 20%), cyclohexane (4.3 ml/min) and an acetic solution of Co acetate tetrahydrate containing 1.1% by weight per weight (flow rate of 3.9 ml/min) are injected continuously.

The injection is continued until a reaction mixture is obtained including approximately 5700 g of adipic acid and consisting of an acetic phase of 35.3 kg and of a cyclohexane phase of 10.3 kg.

The liquid level in the autoclave is kept constant with the aid of a level probe. The reaction mixture is recovered in a glass receptacle heated to 70° C., by virtue of a servo-controlled pneumatic bottom valve.

The separation of the two phases of the reaction mixture obtained is performed at 70° C.

The acetic phase is concentrated to a mass of approximately 19 kg. The adipic acid crystallizes out and is separated off by filtration. It is recrystallized from water (4.2 kg of purified adipic acid are thus obtained).

The mixture of acetic and aqueous solutions originating from the crystallization and from the recrystallization of adipic acid represents approximately 11.5 kg. This mixture is concentrated to approximately 50% of its initial mass and is then diluted with approximately twice its mass of water. A proportion of the cyclohexanone, cyclohexanol and ester compounds is removed by settling and separation.

A hydroacetic solution of the following composition is thus obtained:

| | |
|---|---|
| cobalt | 0.4485% by weight per weight |
| acetic acid | 193 g per kg of solution |
| water | 626 g per kg of solution |
| adipic acid | 41 g per kg of solution |
| glutaric acid | 27.9 g per kg of solution |
| succinic acid | 13.3 g per kg of solution |
| hydroxycaproic acid | 4.8 g per kg of solution |
| hydroxyadipic acid | 9.4 g per kg of solution |
| cyclohexanone | 10.6 g per kg of solution |
| cyclohexanol | 5.7 g per kg of solution |
| cyclohexyl acetate | 3.4 g per kg of solution |
| butyrolactone | 6.4 g per kg of solution |
| valerolactone | 0.8 g per kg of solution |
| various cyclohexyl esters | 41.2 mmol per kg of solution. |

EXAMPLE 3

The electrodialyser employed consists of a stack of 10 cells of 2 dm² active area, each made up of a compartment where the hydroacetic solution to be treated, prepared in Example 2, is introduced (compartment D where the said solution will be dilute in catalyst) and of a compartment C which will receive the cobalt catalyst during the electrodialysis.

The membranes separating each compartment D from the adjacent compartment C are:

anionic membrane of Neosepta AMX brand with quaternary ammonium groups, cationic membrane of Neosepta CMX brand with sulphonate groups.

The electrolyte consists of an aqueous solution of sulphamic acid which has a conductivity of 20 mS/cm at 20° C. The circulation flow rate of this solution is 400 l/h and its volume is 2 l.

The hydroacetic solution to be treated has a volume of 1.6 l (composition shown in Example 2).

The noncontinuous operating method (operation with recirculation) has been employed.

The circulation flow rate of this solution in compartments D is 180 l/h.

The solution which flows in the compartments C and which will receive the cobalt salt is initially an aqueous solution of Co acetate tetrahydrate at a concentration of 10 g/l, to have an initial conductivity of 3.5 to 4 mS/cm; it has a volume of 1.6 l and flows at a flow rate of 180 l/h.

The electrolysis is conducted at an applied voltage of 18 V.

Samples of the various solutions are taken at regular intervals in order to follow the progress of the operation. Cobalt is determined by atomic absorption and the diacids and other organic compounds by vapour phase chromatography. The pH, the conductivity and the volume of the solutions are also followed.

As already reported in Example 1, the feed solution becomes depleted in water; this is explained by the fact that the ions which migrate are hydrated and that at the end of the test the difference in conductivity between the feed solution and the concentrated solution is large (osmosis phenomenon).

To establish precise balances, the results will be expressed in Tables 3 and 4, account being taken of the changes in volume. The results are expressed assuming that initially there is 1 kg of flow to be treated.

Table 3 collates the results relating to the Co catalyst; Table 4 collates the results relating to the organic compounds present in the solution to be treated.

TABLE 3

| Time in min | Solution sampled | Co in mol/kg | Co %/ initial Co in L1 |
|---|---|---|---|
| 0 | L1 | 0.070 | 100 |
| 0 | L2 | 0.026 | 0 |
| 0 | L3 | 0 | 0 |
| 0 | total | 0.096 | |
| 8 | L1 | 0.037 | 53 |
| 9 | L2 | 0.043 | 24.5 |
| 17 | L1 | 0.017 | 24.5 |
| 18 | L2 | 0.061 | 50 |
| 25 | L1 | 0.004 | 6 |
| 26 | L2 | 0.075 | 70 |
| 28 | L1 | 0.002 | 3 |
| 28 | L2 | 0.088 | 88.5 |
| 28 | L3 | 0.006 | 8.5 |
| 28 | total | 0.096 | |

This test on a mixture originating from a test of oxidation of cyclohexane to adipic acid confirms the effectiveness of the isolation of the Co catalyst by electrodialysis.

TABLE 4

| | % remaining relative to the initial solution L1 | | |
|---|---|---|---|
| Compounds | time 0 min | time 17 min | time 28 min |
| adipic acid | 100 | 97.5 | 98.5 |
| glutaric acid | 100 | 95 | 93.5 |
| succinic acid | 100 | 91.5 | 88 |
| hydroxycaproic acid | 100 | 100 | 100 |
| hydroxyadipic acid | 100 | 89 | 88 |
| cyclohexanol | 100 | 96 | 100 |
| cyclohexyl acetate | 100 | 91 | 97.5 |
| cyclohexanone | 100 | 97 | 98 |
| butyrolactone | 100 | 91 | 79 |
| other cyclohexyl esters | 100 | 100 | 100 |
| acetic acid | 100 | 96 | 96 |

The organic compounds remain very predominantly in the feed solution.

EXAMPLE 4

The electrodialyser employed is the same as in the case of Example 3 and the hydroacetic solution to be treated is that which was prepared in Example 2.

The solution which flows in the compartments C and which will receive the cobalt salt is initially the solution L2 obtained in a previous test of electrodialysis of a portion of the solution prepared in Example 2 and the electrolyte solution L3 also originates from this same previous test.

All the application conditions are those of Example 3.

The objective of this test is to show that the concentrated solution of the C compartments can be progressively enriched in Co.

As already reported in Example 1, the feed solution becomes depleted in water; this is explained by the fact that the ions which migrate are hydrated and that at the end of the test the difference in conductivity between the feed solution and the concentrated solution is considerable (osmosis phenomenon).

To establish precise balances, the results will be expressed in Tables 5 and 6, account being taken of the changes in volume. The results are expressed on the assumption that initially there is 1 kg of flow to be treated.

Table 5 collates the results relating to the Co catalyst; Table 6 collates the results relating to the organic compounds present in the solution to be treated.

TABLE 5

| Time in min | Solution sampled | Co in mol/kg | Co %/ initial Co in L1 |
|---|---|---|---|
| 0 | L1 | 0.075 | 100 |
| 0 | L2 | 0.086 | 0 |
| 0 | L3 | 0.010 | 0 |
| 0 | total | 0.171 | |
| 7 | L1 | 0.045 | 60 |
| 8 | L2 | 0.098 | 15.5 |
| 16 | L1 | 0.032 | 43 |
| 17 | L2 | 0.120 | 46 |
| 25 | L1 | 0.012 | 16 |
| 26 | L2 | 0.133 | 63 |
| 30 | L1 | 0.005 | 7 |
| 30 | L2 | 0.153 | 89 |
| 30 | L3 | 0.017 | 9 |
| 30 | total | 0.175 | |

This example with the use of a solution which is already concentrated in Co in the C compartments confirms the efficiency of the isolation of the Co catalyst by electrodialysis and the possibility of obtaining solutions which are still more concentrated in Co.

TABLE 6

| | % remaining relative to the initial solution L1 | | |
|---|---|---|---|
| Compounds | time 0 min | time 16 min | time 30 min |
| adipic acid | 100 | 104 | 95 |
| glutaric acid | 100 | 99.5 | 91.5 |
| succinic acid | 100 | 95 | 83.5 |
| hydroxycaproic acid | 100 | 100 | 99 |
| hydroxyadipic acid | 100 | 100 | 88 |
| cyclohexanol | 100 | 99 | 100 |
| cyclohexyl acetate | 100 | 92.5 | 100 |
| cyclohexanone | 100 | 97 | 100 |
| butyrolactone | 100 | 100 | 100 |
| other cyclohexyl esters | 100 | 100 | 93 |
| acetic acid | 100 | 95 | 95 |

What is claimed is:

1. Process for isolating a homogeneous metal catalyst dissolved in a mixture also containing at least one aliphatic diacid, wherein the catalyst contains cobalt and the isolation is performed by membrane electrodialysis in an electrodialysis apparatus which comprises a stack of a number of cells, each cell comprising two adjacent concentration (C) and dilution (D) compartments bounded alternately by cationic membranes and anionic membranes, wherein said mixture does not contain nitric acid.

2. Process according to claim 1, wherein the catalyst comprises cobalt, alone or with other metals.

3. Process according to claim 2, wherein the metals are in the form of compounds which are soluble in the reaction mixture for cycloalkane oxidation.

4. The process according to claim 2 wherein the other metals comprise manganese, copper, iron, vanadium, cerium or mixtures thereof.

5. Process according to claim 1, wherein the catalyst comprises cobalt salts, alone or in combination with other compounds based on metals.

6. The process according to claim 5, wherein said metals comprise manganese, copper, iron, cerium, vanadium or mixtures thereof.

7. Process according to claim 1, wherein the mixture subjected to the membrane electrodialysis contains at least one diacid formed during the oxidation of the cycloalkane and one or more other diacids also formed as by-products.

8. The process according to claim 7, wherein said diacid comprises adipic acid, glutaric acid or succinic acid.

9. Process according to claim 1, wherein the mixture comprises water, it being possible for the solvent which may have been used in the process which has produced the solution to be treated to be entirely or partially replaced with water before the electrodialysis.

10. Process according to claim 9, wherein water represents from 10% to 100% of the solvent mixture of the solution subjected to the electrodialysis.

11. The process according to claim 10, wherein water represents from 50% to 100% of the solution mixture.

12. Process according to claim 1, wherein the solution which is electrodialysed contains from 0.0001 mole to 1 mole of catalyst per kilogram, from 0.001 mole to 1 mole of glutaric acid per kilogram, from 0.001 mole to 1 mole of succinic acid per kilogram and from 0.001 mole to 1 mole of adipic acid per kilogram.

13. Process according to claim 1, wherein the membranes comprise a matrix onto which functional groups are grafted which are either anionic or cationic.

14. The process according to claim 13, wherein said functional groups comprise sulfonate groups in the case of cationic membranes or quaternary ammonium groups in the case of anionic membranes.

* * * * *